US007471290B2

United States Patent
Wang et al.

(10) Patent No.: US 7,471,290 B2
(45) Date of Patent: Dec. 30, 2008

(54) POSTURE DETECTION SYSTEM

(75) Inventors: Hua Wang, Pasadena, CA (US); John Hatlestad, Maplewood, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 226 days.

(21) Appl. No.: 11/283,489

(22) Filed: Nov. 18, 2005

(65) Prior Publication Data
US 2007/0115277 A1   May 24, 2007

(51) Int. Cl.
*G06T 15/00* (2006.01)

(52) U.S. Cl. .......................... 345/419; 607/19; 607/32; 607/60

(58) Field of Classification Search ................ 345/418, 345/419, 619, 620; 600/300, 585; 607/17–19, 607/32, 60
See application file for complete search history.

(56) References Cited

U.S. PATENT DOCUMENTS

| 5,593,431 | A | 1/1997 | Sheldon | 607/19 |
|---|---|---|---|---|
| 5,935,153 | A | 8/1999 | Legay | 607/18 |
| 5,957,957 | A | 9/1999 | Sheldon | 607/17 |
| 6,044,297 | A | 3/2000 | Sheldon et al. | 607/17 |
| 6,221,011 | B1 | 4/2001 | Bardy | 600/300 |
| 6,277,072 | B1 | 8/2001 | Bardy | 600/300 |
| 6,280,380 | B1 | 8/2001 | Bardy | 600/300 |
| 6,358,203 | B2 | 3/2002 | Bardy | 600/300 |
| 6,368,284 | B1 | 4/2002 | Bardy | 600/508 |
| 6,440,066 | B1 | 8/2002 | Bardy | 600/300 |
| 6,466,821 | B1 * | 10/2002 | Pianca et al. | 607/18 |
| 6,625,493 | B2 | 9/2003 | Kroll et al. | 607/19 |
| 6,658,292 | B2 | 12/2003 | Kroll et al. | 607/19 |
| 6,937,900 | B1 * | 8/2005 | Pianca et al. | 607/19 |
| 7,149,584 | B1 * | 12/2006 | Koh et al. | 607/60 |

* cited by examiner

*Primary Examiner*—Phu K Nguyen
(74) *Attorney, Agent, or Firm*—Hollingsworth & Funk, LLC

(57) ABSTRACT

Methods, systems, and apparatus are described for posture detection. Orientations of a body are detected with respect to first and second axes. A movement of the body with respect to a third axis is also detected. Three-dimensional orientations of the body are determined based on the orientations and the movement. The detected posture may be used for applications such as controlling medical devices and detecting patient disorders.

29 Claims, 12 Drawing Sheets

POSTURE DETECTION SYSTEM

FIELD OF THE INVENTION

The present invention relates generally to medical devices, and more particularly to posture sensing methods and systems.

BACKGROUND OF THE INVENTION

The position or posture of a patient is a factor in various diseases and disorders, including those of the cardiac and/or respiratory systems. Certain disease processes may be exacerbated when the patient assumes particular postures. For example, sleep apnea episodes may begin or increase in frequency or severity when the patient lies down. In another example, congestive heart failure (CHF) patients frequently sleep with their torso tilted upward to reduce pulmonary congestion. Patient posture information may be used to enhance diagnosis of these and other diseases and disorders.

Posture sensing may also be used to enhance therapy delivery, such as cardiac pacing therapy. For example, changes in body posture can cause sudden decrease in blood pressure. For some patients, particularly the elderly and/or people taking certain medications, inadequate neural control of blood pressure may result in syncope upon rising from a sitting position or other sudden posture changes. Posture sensing may be used to improve cardiac pacing therapy during and after posture changes to promote physiologic pacing.

The present invention describes posture detection methods and systems including processes for calibrating and using posture detectors and offers various advantages over the prior art.

SUMMARY OF THE INVENTION

Embodiments of the invention relate to detection of patient posture. In one embodiment of the invention, a method involves detecting orientations of a body with respect to first and second axes. Movement of the body with respect to a third axis is detected, and three-dimensional orientations of the body are detected based on the orientations and the movement. In more particular embodiments, the method also involves detecting steady-state acceleration conditions of the body with respect to the first and second axes. The three-dimensional orientations of the body may be determined for the steady-state acceleration conditions. In a more particular arrangement, determining the three-dimensional position of the body involves determining a sign of the three-dimensional position with respect to the third axis based on transitions between the steady-state acceleration conditions.

In more particular embodiments of the invention, determining the three-dimensional position of the body involves calculating a magnitude component of the three-dimensional position with respect to the third axis using magnitude components of the three-dimensional position with respect to the first and second axes. Detecting the orientation of the body with respect to the first and second axes may involve detecting the orientation using one or more sensors responsive to the earth's gravitational field and/or one or more DC accelerometers. In such a case, the method may also involve determining steady-state acceleration conditions of the body with respect to the first and second axes using AC components extracted from signals of the DC accelerometers.

In other, more particular embodiments of the invention, detecting the movement of the body may involve detecting the movement using one or more AC accelerometers. At least two of the first, second, and third axes may be substantially orthogonal, or at least two of the first, second, and third axes may be non-orthogonal. In one configuration, the body is a patient's body, and at least one of detecting the orientation, detecting the movement, and determining the three-dimensional position may be performed at least in part implantably. The method may also involve controlling a medical device based on the three-dimensional position of the body, such as a cardiac rhythm management device. The method may also involve tracking patient well-being and/or detecting a patient disorder at least in part using the three-dimensional position of the patient's body.

In another embodiment of the invention, an apparatus includes first and second sensors responsive to a gravitational field. The first and second sensors are disposed along respective first and second axes of the apparatus. A movement sensor is disposed along a third axis of the apparatus. Sensing circuitry is coupled to the first and second sensors and the movement sensor. The sensing circuitry is configured to determine orientations of the apparatus with respect to the first and second axes of the apparatus based on outputs of the first and second sensors; determine movements of the apparatus based on outputs of the movement sensor; and determine three-dimensional orientations of the apparatus based on the orientation and the movement.

In more particular embodiments of the invention, the sensing circuitry is further configured to detect steady-state acceleration conditions of the apparatus and determining the three-dimensional orientations of the apparatus for the steady-state acceleration conditions. The apparatus may include control circuitry coupled to the sensing circuitry and configured to receive the three-dimensional orientations of the apparatus and control the apparatus based on the three-dimensional orientations. The apparatus may include cardiac rhythm management circuitry coupled to the control circuitry and configured to adjust a pacing provided by the implantable cardiac rhythm management circuitry based on the three-dimensional orientations of the apparatus received via the control circuitry.

In other, more particular embodiments of the invention, the apparatus may be configured as an implantable medical device. The sensing circuitry may be configured to determine acceleration magnitudes along the third axis based on acceleration magnitudes detected via the first and second sensors, and determine acceleration directions along the third axis based on successive determinations of the acceleration magnitudes along the third axis measured during subsequent steady-state acceleration periods. One or more of the first and second sensors may include DC accelerometers, and the movement sensor may include one or more AC accelerometers. The apparatus may be implanted in a patient's body, and the sensing circuitry configured to determine an orientation of the patient's body based on the three-dimensional orientations of the apparatus.

The above summary of the invention is not intended to describe each embodiment or every implementation of the invention. Advantages and attainments, together with a more complete understanding of the invention, will become apparent and appreciated by referring to the following detailed description and claims taken in conjunction with the accompanying drawings.

Figure 1:
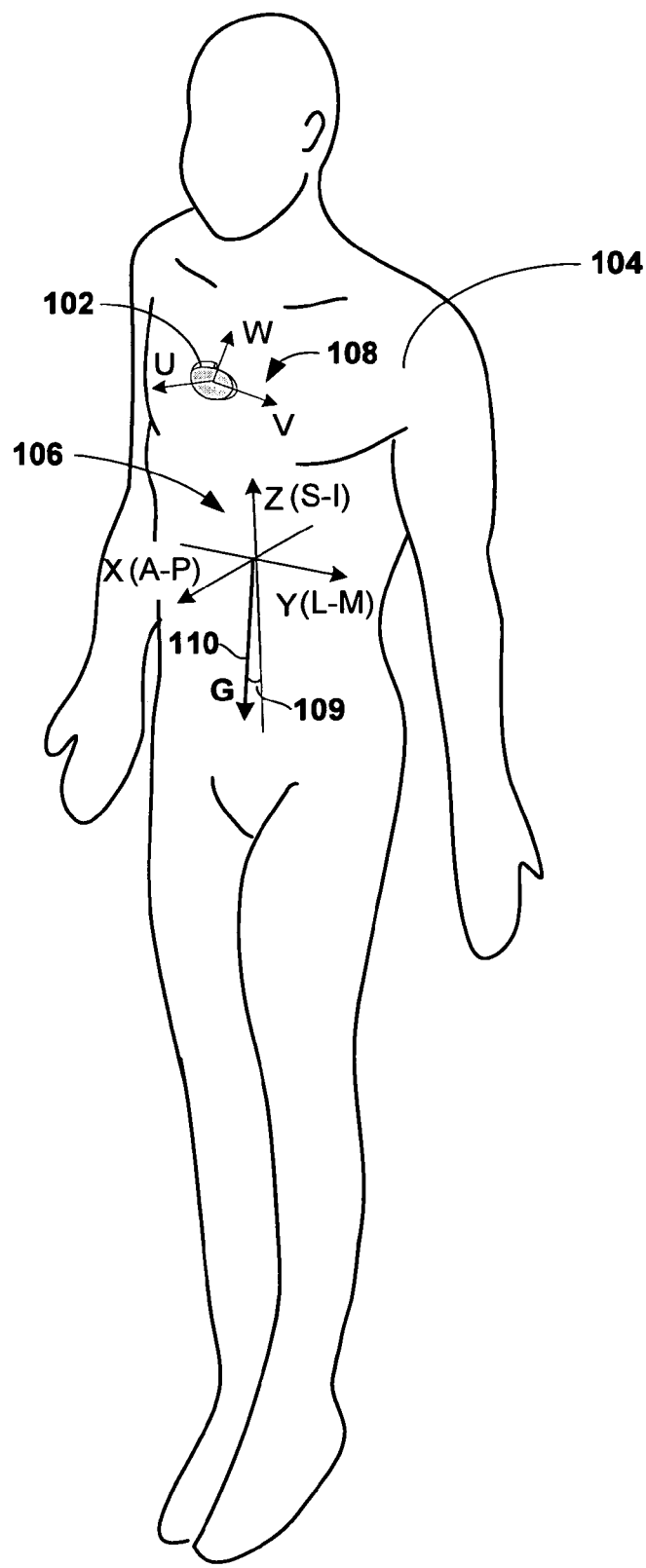
FIG. 1 illustrates a medical device incorporating a posture detector implanted within a patient's body in accordance with an embodiment of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION

In the following description of the illustrated embodiments, references are made to the accompanying drawings which form a part hereof, and in which are shown by way of illustration, various embodiments by which the invention may be practiced. It is to be understood that other embodiments may be utilized, and structural and functional changes may be made without departing from the scope of the present invention.

Patient posture is an important factor in the diagnosis of certain medical disorders and may also be used to enhance therapy delivery. Posture detection involves determining an orientation of the patient's body, such as determining if the patient is in a vertical position (upright or upside down), determining if the patient is in a horizontal position (lying on the back, lying on the stomach, lying on the right side or the left side), or determining if the patient's body is tilted to the right, tilted to the left, tilted forward, or tilted backward. Posture detection in accordance with the embodiments described herein may additionally include determining an angle of tilt of the patient's body. Posture information may be tracked over time, stored, and/or correlated to other medical events.

Information about patient posture may be evaluated with respect to the detection of various disorders to determine if an association between patient posture and a particular disorder is present. The posture of the patient's body, such as the inclination of the upper torso, may be linked to various medical disorders, including disorders affecting the respiratory and/or cardiovascular systems. Tracking patient posture over time can be used to assess the general well-being of a patient. For example, if posture information acquired over a period of time indicates that a patient spends an increasing amount of time lying down and/or inactive, the patient's health may be declining. In another example, if the patient's posture indicates a change in sleeping position, such as a shift from sleeping lying down to sleeping sitting up, this change may indicate increased pulmonary congestion related to congestive heart failure (CHF). In yet another example, discriminating between a recumbent and an upright position of the patient's body is useful in determining if a patient is asleep or awake. Diagnosis of various conditions, e.g., sleep apnea, may be enhanced with knowledge of the patient's sleep state. Thus, a patient may be diagnosed as having sleep disordered breathing if breathing interruptions occur while a patient is sleeping, as indicated by patient posture during the disordered breathing episodes.

Knowledge of patient posture may also be used to deliver therapy appropriate to the patient's particular situation. For example, posture information may be used by a cardiac rhythm management (CRM) device with or without information the activity level of the patient so that cardiac pacing is delivered at a hemodynamically appropriate pacing rate. In another implementation, cardiac pacing may be adjusted if a sudden change in the patient's posture is detected. In yet another implementation, cardiac and/or other types of therapy may be adjusted to accommodate the patient's sleep/wake cycle as determined, at least in part, by the patient posture. For example, a cardiac pacing rate may be decreased from a waking rate to a lower sleeping rate to account for the decreased hemodynamic need of the patient during sleep.

Methods and systems described herein, in accordance with embodiments of the invention, provide for improvements in multi-axis posture detection. The apparatus used for posture detection utilizes combinations of sensors responsive to gravitational fields and motion sensors. An example of the former sensor is a DC accelerometer, and an example of the latter is an AC accelerometer. Although the embodiments of gravitational field and motion detectors are generally described herein in terms of DC and AC accelerometers, those of skill in the art will appreciate that alternate sensing technologies may be utilized. For example, technologies such as mechanical sensors (e.g., ball-in-cup sensor), mercury switches, absolute position sensing, Doppler radio detection, laser inferometry, gyroscopes, electronic compasses, and the like may be adapted to perform any combination of gravitational field and movement detection.

Generally, a DC accelerometer refers to a device that can measure static acceleration (i.e., 0 Hz events). For example, piezo-resistive and capacitive accelerometers are capable of measuring static acceleration. In contrast, piezo-electric accelerometers generally cannot measure static events; they need motion (AC acceleration) to provide an output. The output of this type of accelerometer decreases the closer that the rate of change in acceleration approaches zero.

In one implementation of the invention, determining patient posture involves taking measurements from a two-dimensional DC accelerometer mounted along two axes of an implantable device. An AC accelerometer is mounted along the third axis of the device. Based on the measurements from these accelerometers, the three steady-state components of the gravitational acceleration vector G in device coordinates can be inferred. These vectors in device coordinates can then be used to determine the patient's posture relative to the earth's surface.

Typically, the accelerometers in a device are mounted relative to a predetermined coordinate system of the device. The device is usually designed to be implanted in an orientation that is approximately aligned with a body coordinate system. However, even when such a device is carefully implanted into a person, there may still be angular offsets between the device coordinates and the body coordinates. The acceleration relative to body coordinates is the important measurement for determining posture of a patient. Therefore, a transformation matrix between the device coordinates (used for measuring the acceleration signals) and the body coordinates (used for determining postures) can be determined during a calibration process after device implantation. Postures and activities relative to the patient's body can thereafter be inferred by applying the transfer matrix on the acceleration components measured in device coordinates.

FIG. 1 illustrates a medical device 102 that incorporates a posture detector according to an embodiment of the invention. The device may be implanted within a patient's body 104 in the upper left thoracic region, such as a typical placement for a cardiac pacemaker or defibrillator. The medical device 102 includes hardware and software capable of accurately measuring a patient's posture. The term posture as used herein generally refers to the orientation of the patient's torso relative to the earth's surface. However, those skilled in the art will appreciate that the methods and apparatus associated with the posture sensing medical device 102 may be applicable to position measurement of any body part, as well as being applicable to analogous applications that require detecting relative orientation of devices and/or movable bodies.

As shown in FIG. 1, the position of the patient's body 104 may be expressed in terms of body coordinates 106 having axes X, Y, and Z. The reference axes for the body coordinate system may be selected to be mutually orthogonal, although non-orthogonal reference axes may alternatively be selected. In one implementation, illustrated in FIG. 1, the X axis of the body coordinate system 106 generally corresponds to the anterior-posterior (A-P) axis of the body, the Y axis generally corresponds to the lateral-medial (L-M) axis of the body, and the Z axis generally corresponds to the superior-inferior (S-I) axis of the body.

The posture detector of the medical device 102 is associated with device coordinate 108 axes U, V, and W. Each axis, U, V, or W, of device coordinate system 108 corresponds to a direction in which the posture detector detects acceleration, e.g., by having the sensitive axis of an accelerometer aligned in that direction. As with the body coordinate system 106, the device coordinate system 108 is also typically selected to have mutually orthogonal axes. Generally, the implantable device 102 is designed to be implanted such that its local U-V-W coordinate system 108 is approximately aligned to the patient's X-Y-Z coordinate system 106, which itself is chosen to be roughly aligned with the gravitational vector G 110 while the patient is standing or lying down. However, as can be observed in FIG. 1, the sensitive axes of the uniaxial accelerometers U, V, and W may not necessarily be closely aligned with body coordinates X, Y, and Z. Further, the device axes U, V, and W may not be aligned perfectly with respect to the gravitational acceleration vector G acting on the patient's body 104. In a typical implant implementation, the device axes are tilted slightly or significantly with respect to the vector G.

The gravitational vector G 110 is used to designate the direction and magnitude of the force of gravity acting on the patient's body. The position of the patient's body may be expressed in body coordinates 106 by translating the gravitational force vector G acting on the patient's body from device coordinates 108 (U,V,W) to body coordinates 106 (X,Y,Z). Embodiments of the invention may involve directly determining the transfer matrix for translating device coordinates 108 (U,V,W) to body coordinates 106 (X,Y,Z).

In one implementation, the medical device 102 detects acceleration using a plurality of uniaxial accelerometers aligned with two or more axes of the device coordinate system 108. These accelerometers may be formed as an integrated device such as a surface micro-machined semiconductor device. For example, each uniaxial accelerometer may comprise an inertial mass suspended by compliant springs which are acted on by gravity. The magnitude of the inertial mass deflection is converted to an electrical signal by the surrounding electronics and appears as the sensor output of the uniaxial accelerometer. The output of an accelerometer acted on by the earth's gravitational force provides a characteristic output voltage, e.g., maximum output, if the sensitive axis of the accelerometer is aligned with the earth's gravitational field. As the patient's body moves, the angle at which the sensitive axis of the accelerometer is tilted with respect to the earth's gravitation force changes and the output of the accelerometer is related to the angle of tilt.

In conventional systems, one three-dimensional (3D) DC accelerometer is used to detect the postures and another AC accelerometer is aligned with the anterior-posterior axis to measure the activity level. However, the strategy of one 3D DC accelerometer plus one AC accelerometer may be difficult to implement and may not be reliable over the long term. In addition, due to imperfections inherent in the calibration process, the prediction of postures is not sufficiently sensitive and has often been biased by calibration errors.

Another known approach to posture detection involves using only a single 2D DC accelerometer which can detect postures including standing, prone, lying on the left, supine, and lying on the right. However, due to limited inputs, the system can only distinguish different posture clusters on a two-dimensional plane. Thus, resolution and precision are sacrificed. What is more, how those posture clusters are distributed depends on the device orientation during implantation. This also affects the system reliability for practical applications.

Figure 2:
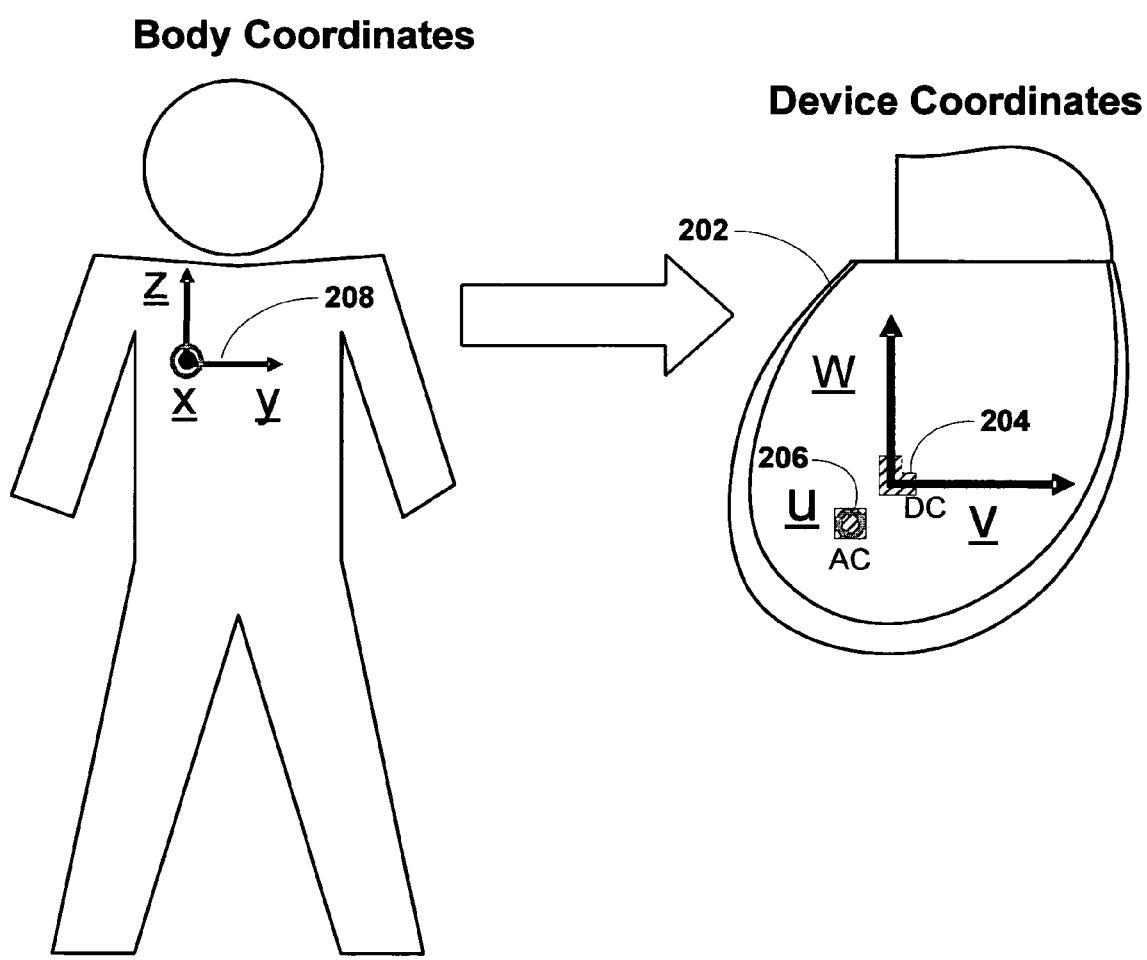
FIG. 2 illustrates the body coordinate system X,Y,Z, device coordinate system U,V,W and associated orientation of a posture detector in accordance with embodiments of the invention.

The present disclosure is directed to a new strategy of implanted hardware system design and associated software design that detects posture with greater precision than conventional approaches. FIG. 2 shows an implantable apparatus 202 with posture detection according to embodiments of the invention. The apparatus 202 includes one 2D DC accelerometer 204 that is implemented along the V and W directions in the device coordinates. Another AC accelerometer 206 is mounted along the third axis (U direction). The 2D DC accelerometer 204 will record the components of gravitational acceleration G in the V and W directions. Because the vector sum of the U, V, and W signals is the total G, the following equations hold:

$$g = \sqrt{u^2 + v^2 + w^2} \quad (1)$$

$$|u| = \sqrt{g^2 - v^2 - w^2} \quad (2)$$

Based on equations (1) and (2) above, the magnitude of the U-gravitation component can be inferred during steady-state acceleration conditions because, for most practical purposes, g is a known constant during steady-state. By analyzing the AC signal recorded in the U direction by the implanted AC accelerometer 206 during unsteady-states, the sign of the U gravitational component can be determined at each successive period of steady-state acceleration. Thus, using only the 2D DC accelerometer 204 and single-axis AC accelerometer 206, the magnitude and direction of the U component can be determined. By using a transfer matrix determined during the calibration process, the steady-state gravitational vector components can then be converted to body coordinates 208. A more detailed description of this calibration process is described in commonly owned U.S. Publication No. 2007/0118056 (hereinafter referred to as the "CALIBRATION" reference), which is hereby incorporated by reference in its entirety.

Using accelerometers 204, 206 as described in relation to FIG. 2, a tilting angle relative to G can be calculated to a resolution of about 5 degrees. The tilting angle (e.g., angle 109 in FIG. 1) with respect to the Z direction can be calculated as follows:

$$\theta = \cos^{-1}\left(\frac{-z}{\sqrt{x^2 + y^2 + z^2}}\right) \quad (3)$$

The tilting angle derived in equation (3) is applied to spherical surface threshold regions in order to determine the posture of the subject at any given time, as described more fully in the "CALIBRATION" reference.

Figure 3:
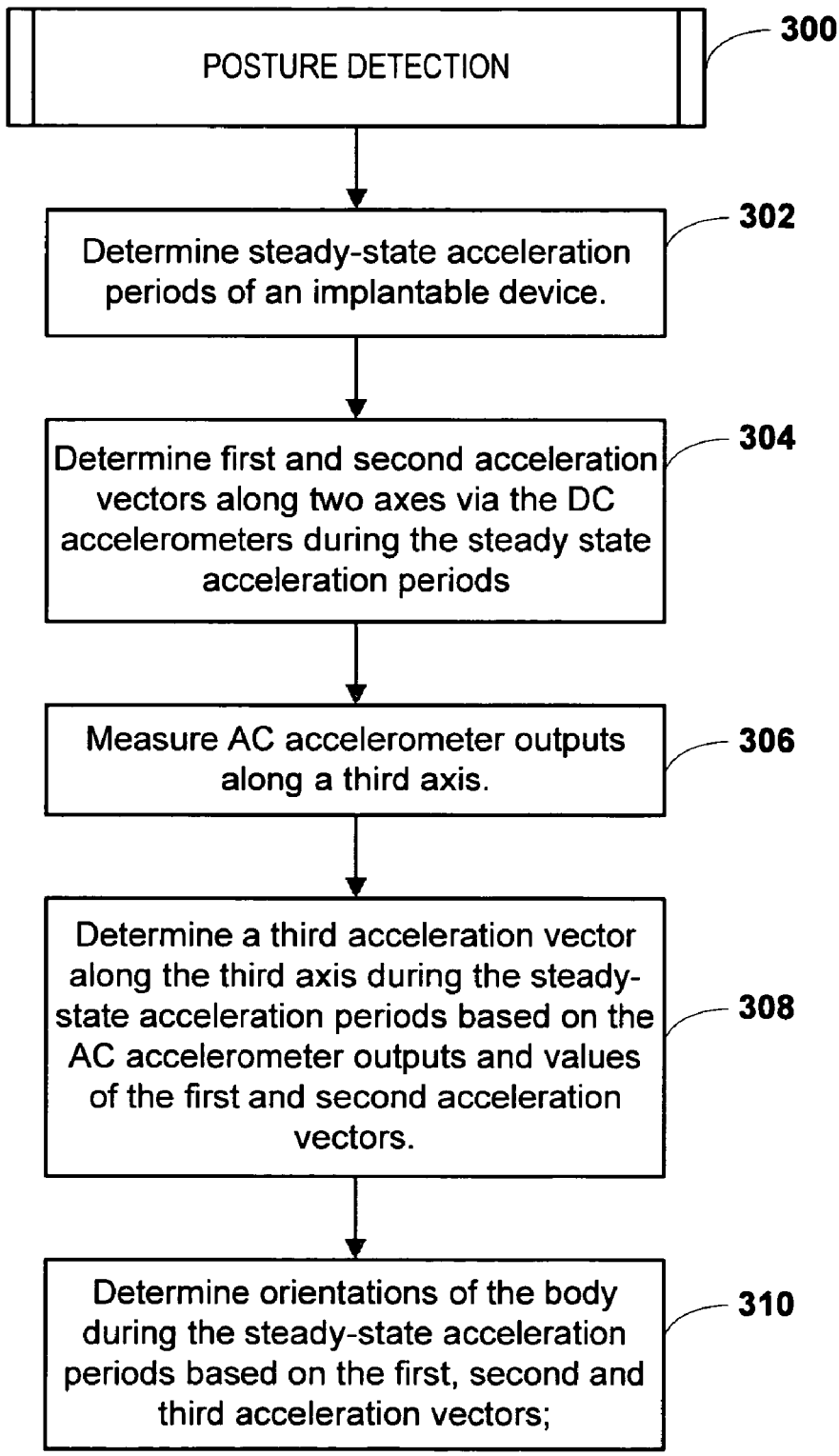
FIG. 3 is a flowchart illustrating a method for posture detection in accordance with embodiments of the invention.

In reference now to FIG. 3, a general procedure 300 for deriving steady-state acceleration components in device coordinates is illustrated in accordance with an embodiment of the invention. The procedure 300 involves determining 302 steady-state acceleration periods of an implantable device. Generally, the derivation of posture assumes that the device (and thus the patient) is experiencing a constant acceleration equal to G, and this is true when the patient is relatively still. During these steady-state periods, the gravitational vectors from the DC accelerometers are determined 304 along two axes (typically the V and W device axes).

The outputs of the AC accelerometer are also measured 306 along a third axis (e.g., the U device axis). During the steady-state periods, the third acceleration vector (e.g., the U-component of acceleration) is determined 308 based on the AC accelerometer outputs and the values of the first and second acceleration vectors. The magnitude of the third vector is determined 308 using equation (2) and the magnitudes of the first and second acceleration vectors. As will be described more fully hereinbelow, the direction of the third vector is determined 308 based on integration of the AC accelerometer outputs during unsteady-state periods that occur between successive steady-state periods.

Once the magnitude and direction of the third acceleration vector is determined 308, the orientation of the body is determined 310 based on the three vectors. For example, a tilt angle can be calculated such as in equation (3). This tilt angle can be calculated relative to the local, device coordinates or another coordinate system (e.g., body coordinates). For an implantable device, the orientation may be expressed relative to a body coordinate by first performing a transform on the three components that were measured relative to the device coordinates. The tilt angle is then calculated and expressed relative to body coordinates. The orientations of the device determined as described above may be applied, either directly or indirectly, to control a device. For example, the pacing rate of a cardiac rhythm management device may be adjusted in response to detected orientations. The orientations may also be used either alone or in conjunction with other medical sensors to monitor patient's health and/or status, detect diseases, and related uses.

Figure 4:
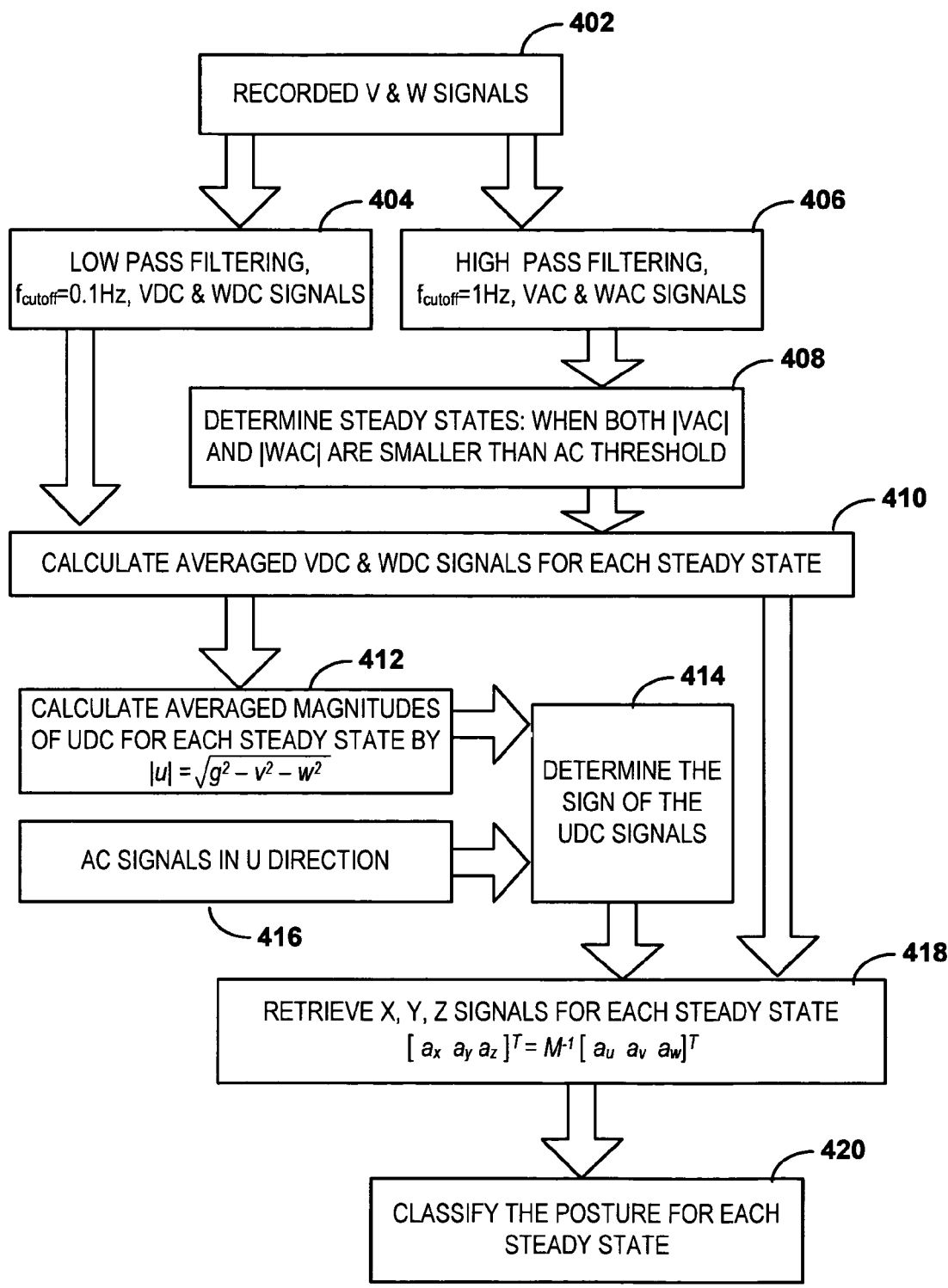
FIG. 4 is a block diagram illustrating a more particular posture detection procedure according to an embodiment of the invention.

A more detailed procedure for measuring posture and activity according to an embodiment of the invention is shown in FIG. 4. The procedure begins with the recording 402 of acceleration signals in the V and W directions via a 2D DC accelerometer. The signals are low-pass filtered 404 to extract the static component of acceleration, referred to herein as VDC and WDC. In the illustrated example, the VDC and WDC signals are obtained with a low-pass cutoff frequency of 0.1 Hz.

The V and W acceleration signals are high-pass filtered 406 to extract the dynamic component of acceleration, referred to herein as VAC and WAC. The high pass cutoff frequency in this example is 1 Hz. The magnitudes of VAC and WAC taken from the high-pass filter 406 are used to determine steady-states 408. Generally, this determination 408 involves multiplying the magnitudes of VAC and WAC signals a by a constant factor and comparing this result with an AC threshold. For the purposes of posture detection in a patient, the signals may be compared to an empirically determined threshold of about 0.02. The system is considered to be in a steady-state at any time that the magnitude of both VAC and WAC are smaller than the AC threshold. In other embodiments, the AC signal in the U direction, UAC, may be used instead of, or in addition to the VAC and WAC components to determine the steady-state condition.

Within each steady-state, an averaged value of VDC and WDC is calculated 410. The magnitude of the U component of acceleration (UDC) can also be calculated 412 using equation (2) given above. The sign of UDC can then be determined 414 using the calculated magnitude of UDC and AC signals recorded 416 in the U direction. Details on determining the sign of UDC are provided in greater detail in connection with FIGS. 4 and 5 of the present specification. Once the sign of UDC is determined 414 the acceleration components in the X, Y, and Z body coordinates are determined 418. This determination involves the use of the inverse transfer matrix M. The value of M is determined during the calibration process. The determination 418 of acceleration components in the X, Y, and Z coordinates are governed by the equations below:

$$\begin{bmatrix} a_u \\ a_v \\ a_w \end{bmatrix} = M \begin{bmatrix} a_x \\ a_y \\ a_z \end{bmatrix} = \begin{bmatrix} M_{11} & M_{12} & M_{13} \\ M_{21} & M_{22} & M_{23} \\ M_{31} & M_{32} & M_{33} \end{bmatrix} \begin{bmatrix} a_x \\ a_y \\ a_z \end{bmatrix} \quad (4)$$

$$\begin{bmatrix} a_x \\ a_y \\ a_z \end{bmatrix} = M^{-1} \begin{bmatrix} a_u \\ a_v \\ a_w \end{bmatrix} \quad (5)$$

After the acceleration components in the X, Y, and Z direction are calculated 418, the posture for each steady-state can be classified 420. The determination of the transfer matrix M during calibration may be acquired by various methods. One example of determining the transfer matrix is described in the "CALIBRATION" reference, as is the posture classification 420 based on X, Y, and Z acceleration components.

Figure 5:
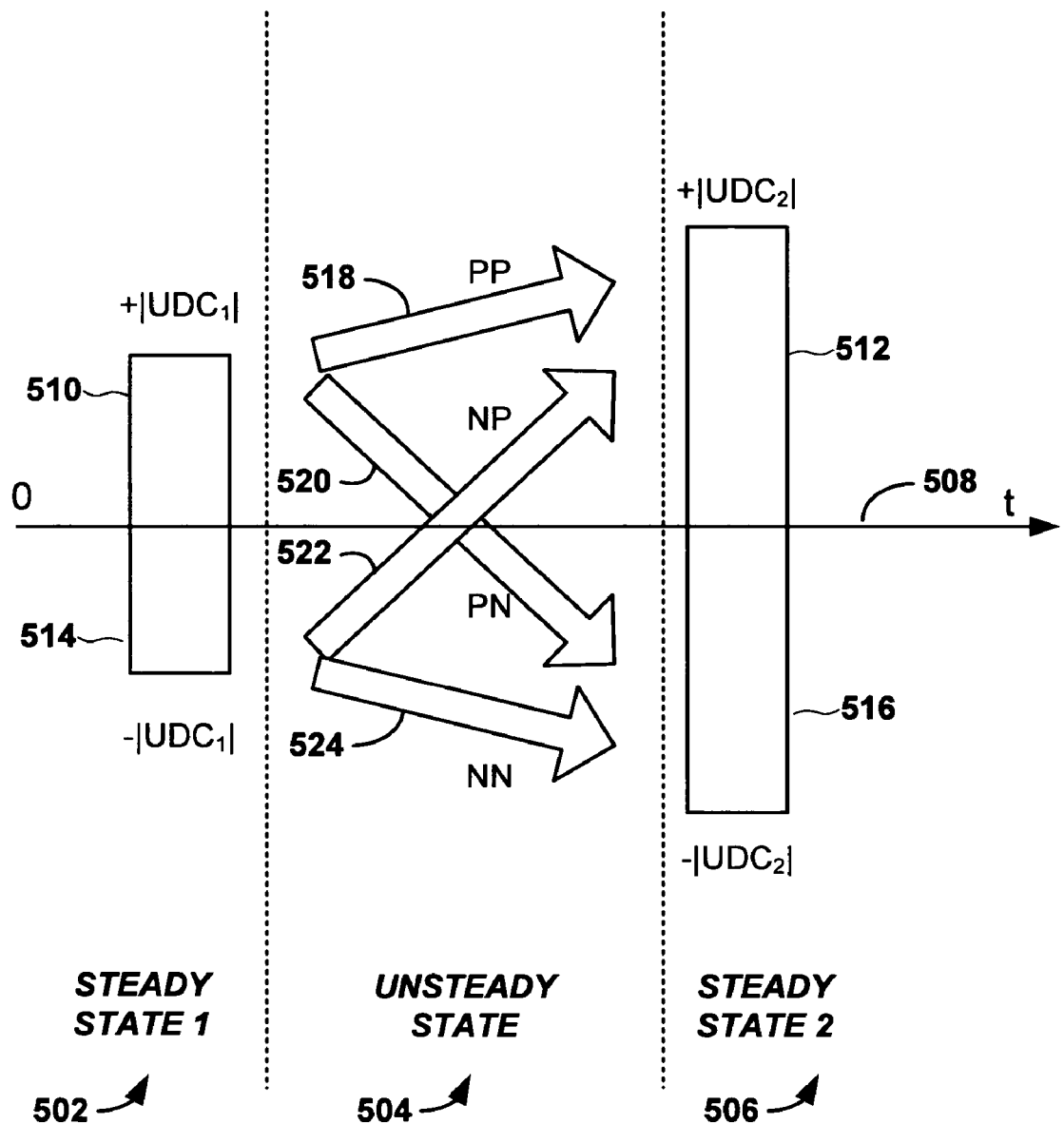
FIG. 5 is a block diagram illustrating U-component acceleration direction changes between successive steady-states according to embodiments of the invention.

A more detailed procedure for determining 414 of the sign of UDC is illustrated in FIG. 5, which is a block diagram showing state changes of a system according to embodiments of the invention. As described above in relation to FIG. 4, the system is considered at steady-state when the AC component of the V and W acceleration satisfies a threshold value. A transition between different periods of steady-state acceleration is shown in FIG. 5, where the system successively transitions between two steady-states 502, 506, with an unsteady-state 504 therebetween. The time axis 508 indicates the direction of increasing time.

For each of the steady-states 502, 506, the sign of UDC may be positive (as indicated by regions 510, 512, respectively) or negative (as indicated by regions 514, 516, respectively). Therefore, there are four possibilities for sign changes between successive steady-states 502, 506, as indicated by arrows 518, 520, 522, and 524. Arrow 518 is labeled PP and represents $+|UDC_1| \rightarrow +|UDC_2|$; arrow 520 is labeled PN and represents $+|UDC_1| \rightarrow -|UDC_2|$; arrow 522 is labeled NP and represents $-|UDC_1| \rightarrow +|UDC_2|$; and arrow 524 is labeled NN and represents $-|UDC_1| \rightarrow -|UDC_2|$.

Figure 6:
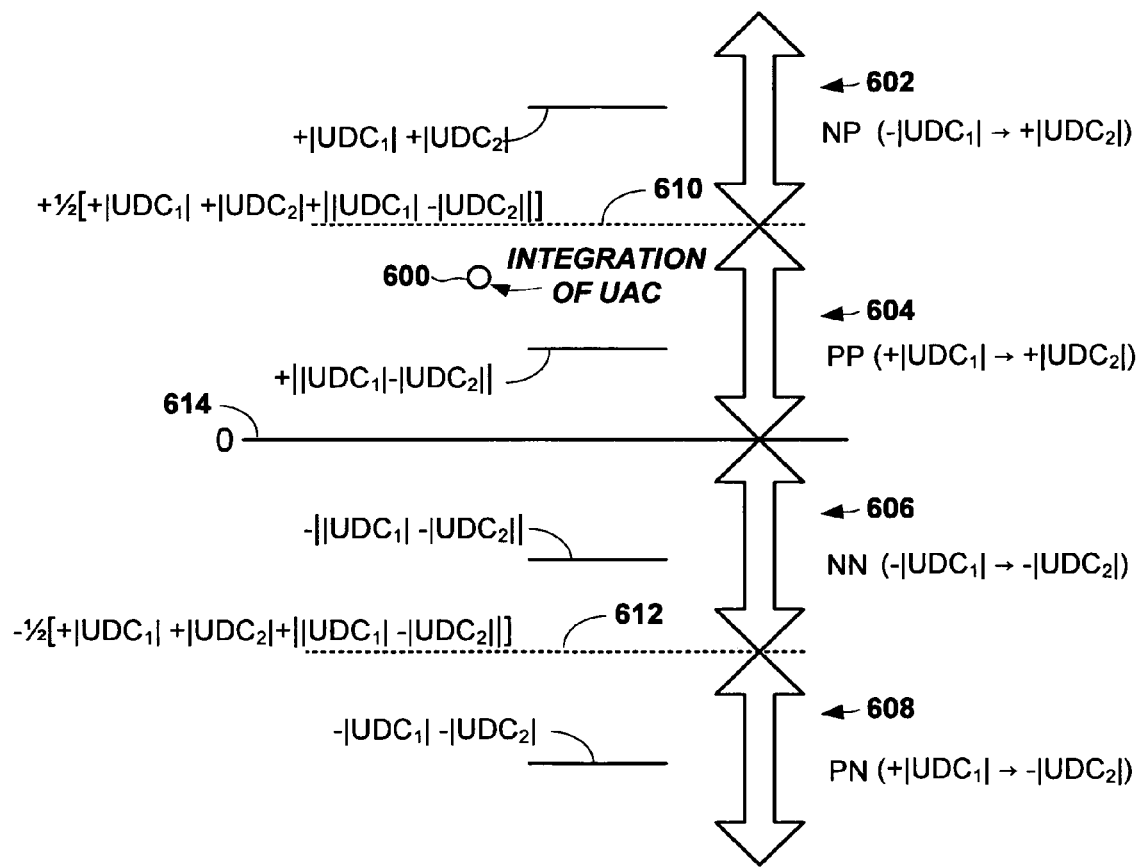
FIG. 6 is a block diagram of threshold values for determining U-component acceleration direction changes between successive steady-states according to embodiments of the invention.

The determination of sign change between successive steady-states 502, 506 involves integrating the value of UAC during the unsteady-state 504. The result of this integration, referred to hereinbelow as UACIntegration, is used to detect the sign/direction of UDC as further explained in FIG. 6. FIG. 6 is a block diagram illustrating sign change determination for various values of UACIntegration. If the value of UACIntegration lies within four regions 602, 604, 606, and 608 shown in FIG. 5, then the steady-state sign change of UDC is determined to be NP, PP, NN and PN, respectively.

The boundary 610 between regions 602 and 604 is $\frac{1}{2}[|UDC_1|+|UDC_2|+||UDC_1|-|UDC_2||]$ and the boundary 612 between regions 606 and 608 is $-\frac{1}{2}[|UDC_1|+|UDC_2|+||UDC_1|-|UDC_2||]$. The boundary 614 between regions 604 and 606 is zero. Therefore, the determination of sign change between successive steady-states can be summarized as follows:

If $0 \leq$ UACIntegration $\leq \frac{1}{2}[|UDC_1|+|UDC_2|+||UDC_1|-|UDC_2||]$, then UDC sign change is $+|UDC_1| \rightarrow +|UDC_2|$, PP;

else if $\frac{1}{2}[|UDC_1|+|UDC_2|+||UDC_1|-|UDC_2||]<$ UACIntegration, then UDC sign change is $-|UDC_1| \rightarrow +|UDC_2|$, NP;

else if $-\frac{1}{2}[|UDC_1|+|UDC_2|+||UDC_1|-|UDC_2||] \leq$ UACIntegration $<0$, then UDC sign change is $-|UDC_1| \rightarrow 1|UDC_2|$, NN;

else if UACIntegration $< -\frac{1}{2}[|UDC_1|+|UDC_2|+||UDC_1|-|UDC_2||]$, then UDC sign change is $+|UDC_1| \rightarrow 1|UDC_2|$, PN.

The above result can be normalized by defining a variable K and noting, that if integration of UAC is positive, K is defined by:

$$UAC\text{Integration}=K(+|UDC_1|+|UDC_2|)+(1-K)||UDC_1|-|UDC_2|| \quad (6)$$

However, if integration of UAC is negative, then K is defined by:

$$UAC\text{Integration}=-K(+|UDC_1|+|UDC_2|)-(1-K)||UDC_1|-|UDC_2|| \quad (7)$$

Thus, K and 1−K are coefficients when UACIntegration is linearly expressed by $+(|UDC_1|+|UDC_2|)$ and $+||UDC_1|-|UDC_2||$ or $-(|UDC_1|+|UDC_2|)$ and $-||UDC_1|-|UDC_2||$. If K=1, this means it can be determined with certainty that UACIntegration$=+(|UDC_1|+|UDC_2|)$ or UACIntegration$=-(|UDC_1|+|UDC_2|)$, thus corresponding to respective sign changes NP or PN. Similarly, if K=0, it can determined with certainty that UACIntegration$=||UDC_1|-|UDC_2||$ or UACIntegration$=-||UDC_1|-|UDC_2||$, corresponding to respective sign changes PP or NN. However, if K=½ then UACIntegration$=\frac{1}{2}[|UDC_1|+|UDC_2|+||UDC_1|-|UDC_2||]$ or UACIntegration$=-\frac{1}{2}[|UDC_1|+|UDC_2|+||UDC_1|-|UDC_2||]$. In such a case, the value of UACIntegration is on one of the two threshold lines 610, 612, and a determination of sign change cannot be made with certainty. Thus, the sign change of UDC between successive steady-states can be determined with greater certainty the further that K is away from 0.5.

Because a sign change can be detected for each steady-state pair, the succeeding sign detection is actually independent of the preceding sign detection. This can prevent forward propagation of sign detection errors from previous steady-state pairs as follows. For the same steady-state, different signs may be predicted from the two steady-state pairs of which it is a part. In that case, a comparison of K values can be made for the two conflicting sign detections. The certainty of the final sign detection decision can be maximized by choosing the sign determination whose value is furthest away from 0.5.

Even with this optimization, it will be appreciated that when the UDC signal is fluctuating around a certain value with the possible postures of Walking and Sleeping, sign detection with the K method may fail and result in errors. To prevent this result, a "Big Steady-state" procedure is defined hereinbelow. If two adjacent UDC signal magnitudes are very close to each other, then UACIntegration magnitude value is eventually relatively small (much smaller than the sum of the two UDC magnitudes), and the two adjacent UDC measurements are considered to have the same sign. These two states are joined together and considered as a Big Steady-state with undetermined sign. If the next UDC magnitude is still close (thus UACIntegration is still small) the next steady-state will also be appended onto the Big Steady-state. In one embodiment, the Big Steady State ends when two adjacent UDC signal values are no longer close to each other. Until the Big Steady-state ends, its sign can be determined by taking it as an ordinary steady-state and detecting it with the two adjacent steady-states. This "Big Steady-state" will help detect the UDC sign when the UDC signal is fluctuating, and thus remove invalid transitions, such as transitions from NN to PP, and vice versa.

Figure 7:
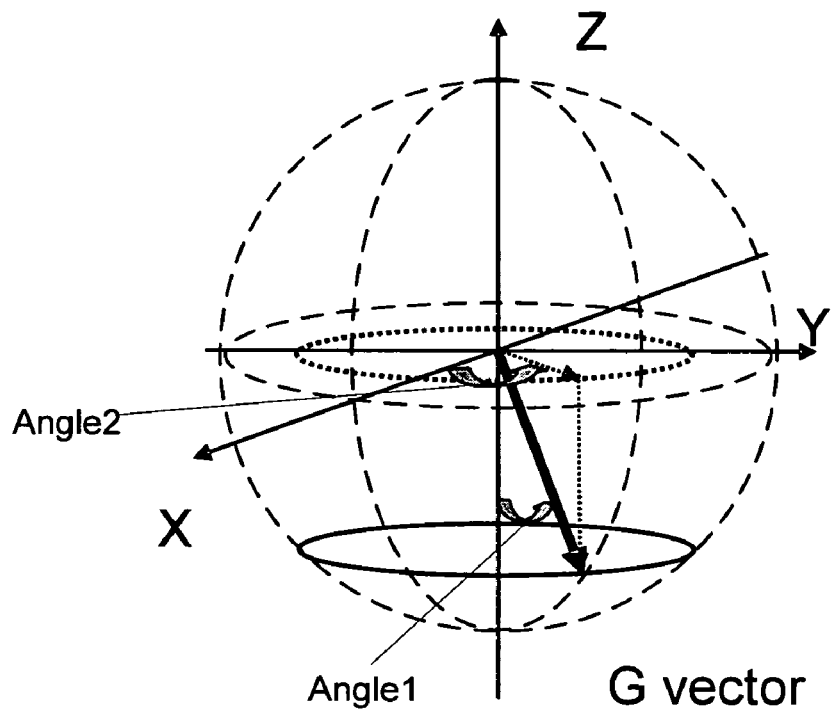
FIG. 7 illustrates a spherical gravitational G vector surface used for posture detection in accordance with embodiments of the present invention.

Once orientations of the patient are detected, these orientations may be used to determine the patient's posture in terms useful for medical diagnosis and treatment (e.g., standing, supine, etc). Posture sensing methods in accordance with embodiments of the present invention are based on the use of a spherical gravitational G vector surface. As illustrated in FIG. 7, when the body coordinate system is chosen as the reference coordinate system, the gravitational acceleration vector G for any possible posture may be mapped to a certain point on a spherical surface, with radius the magnitude of the G vector. The orientation of the G vector can be determined by two rotational angles, designated Angle1 and Angle2. In the example depicted in FIG. 4, Angle1 is defined as the polar angle between the vector G and the negative Z direction. Angle2 is defined as the azimuthal angle between the projected vector G on the X/Y plane and the positive X axis.

Mathematically, Angle1 may be calculated as follows:

$$Angle1 = \arccos\left(\frac{-z}{\sqrt{x^2 + y^2 + z^2}}\right) \quad (8)$$

Angle2 may be calculated, $$Angle2 = a\cos\left(\frac{x}{\sqrt{x^2 + y^2}}\right), \text{ if } y > 0, \quad (9)$$

and, $$Angle2 = -a\cos\left(\frac{x}{\sqrt{x^2 + y^2}}\right), \text{ if } y < 0. \quad (10)$$

Angle1 and Angle2 provide detailed information about the patient postures and may be defined as the quantitative outputs for posture classification. For example, based on Angle 1 and Angle 2, the posture sensing device may report four or more intermediate tilting postures such as Tilting forward, Tilting Backward, Tilting Right and Tilting Left.

Figure 8A:
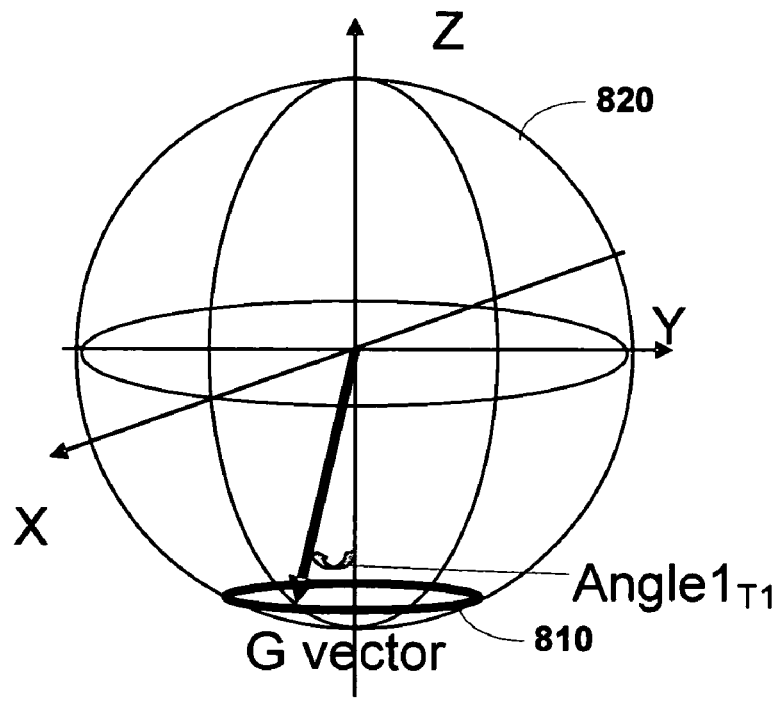
FIG. 8A illustrates a first threshold region defined by a first threshold angle, $Angle1_{T1}$, in accordance with embodiments of the invention.
Figure 8B:
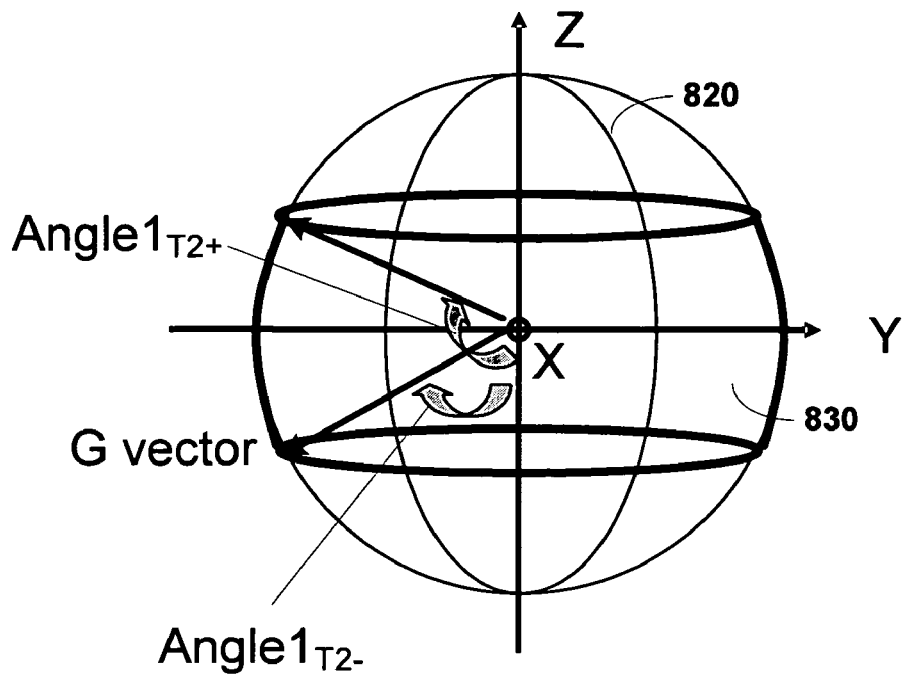
FIG. 8B illustrates a second threshold region defined by a second threshold angle, $Angle1_{T2}$, in accordance with embodiments of the invention.

Posture determination may be achieved by setting up threshold regions on the G vector spherical surface corresponding to various postures. For example, threshold regions may be defined as illustrated in FIGS. 8A and 8B. FIG. 8A illustrates a first threshold region 810 which corresponds to the intersection of a cone surface defined by a threshold angle, Angle1$_{T1}$ and the total spherical G vector surface 820. If the G vector is pointing in threshold region 810, then the patient's posture is classified as standing/sitting upright.

FIG. 8B provides a view, looking through the X axis, of the G vector surface 820. A second threshold region 830 is defined as a ring section along the equator of the G vector surface 810 defined by the threshold angles, Angle1$_{T2-}$ and Angle1$_{T2+}$, between the G vector and the −Z axis. If the G vector is pointing in threshold region 830, then the posture is classified as lying down.

Figure 8C:
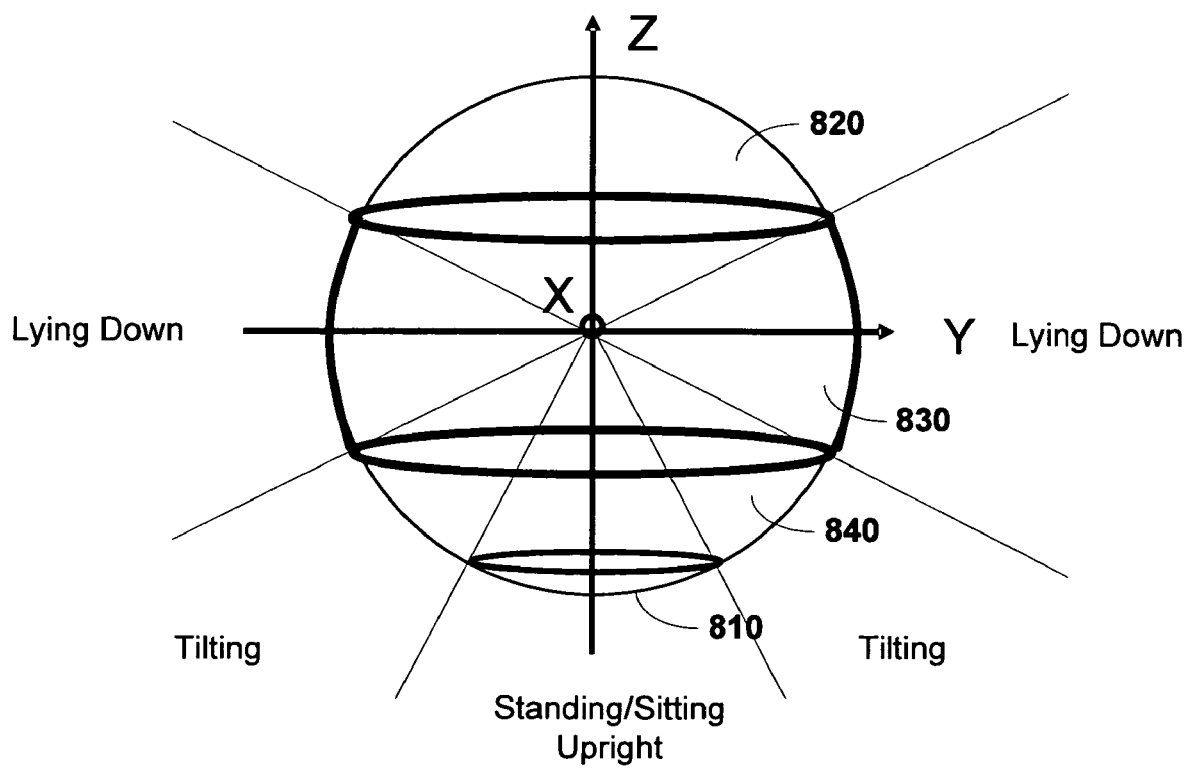
FIG. 8C illustrates possible patient postures including a standing/sitting upright posture, a lying down posture, and a tilting posture.

Looking through the X axis, FIG. 8C illustrates possible patient postures including a standing/sitting upright posture, a lying down posture, and a tilting posture. If the G vector points in the first threshold region 810, then the patient is classified as having a standing/sitting upright posture. If the G vector points in the second threshold region 830, then the patient is classified as having a lying down posture. FIG. 8C shows an intermediate tilting section 840 between the first threshold region 810 and the second threshold region 830. If the G vector points in the intermediate section 840, then the patient classified as having a tilting posture.

Figure 9:
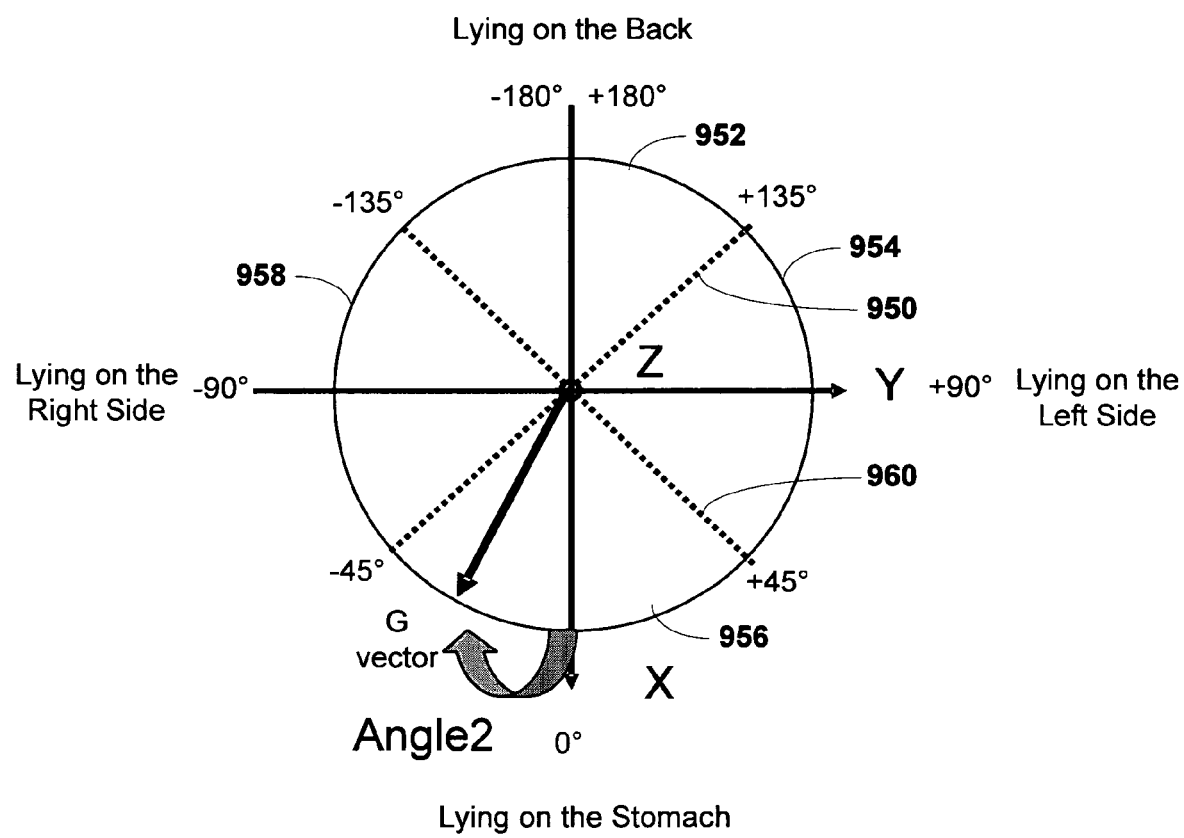
FIG. 9 illustrates four posture detection regions in accordance with embodiments of the invention.

FIG. 9 shows a view of the G vector surface looking through the Z axis. As depicted in FIG. 9, the Lying down region 830 (FIG. 8C) and the Tilting region 840 (FIG. 8C) can be subdivided into four parts 952, 954, 956, 958, for example, by 45° lines 950 and 960. Angles other than 45° may alternatively be used to subdivide the tilting region. When the G vector points in section 956 along the positive X direction, the patient is lying on his/her stomach or tilting forward. When the G vector points in section 952 along the negative X direction, the patient is lying on his/her back or tilting backward. When the G vector points in section 954 along the positive Y direction the patient is lying on his/her left side or tilting left. When the G vector points in section 958 along the negative Y direction, the patient is lying on his/her right side or tilting right.

Figure 10:
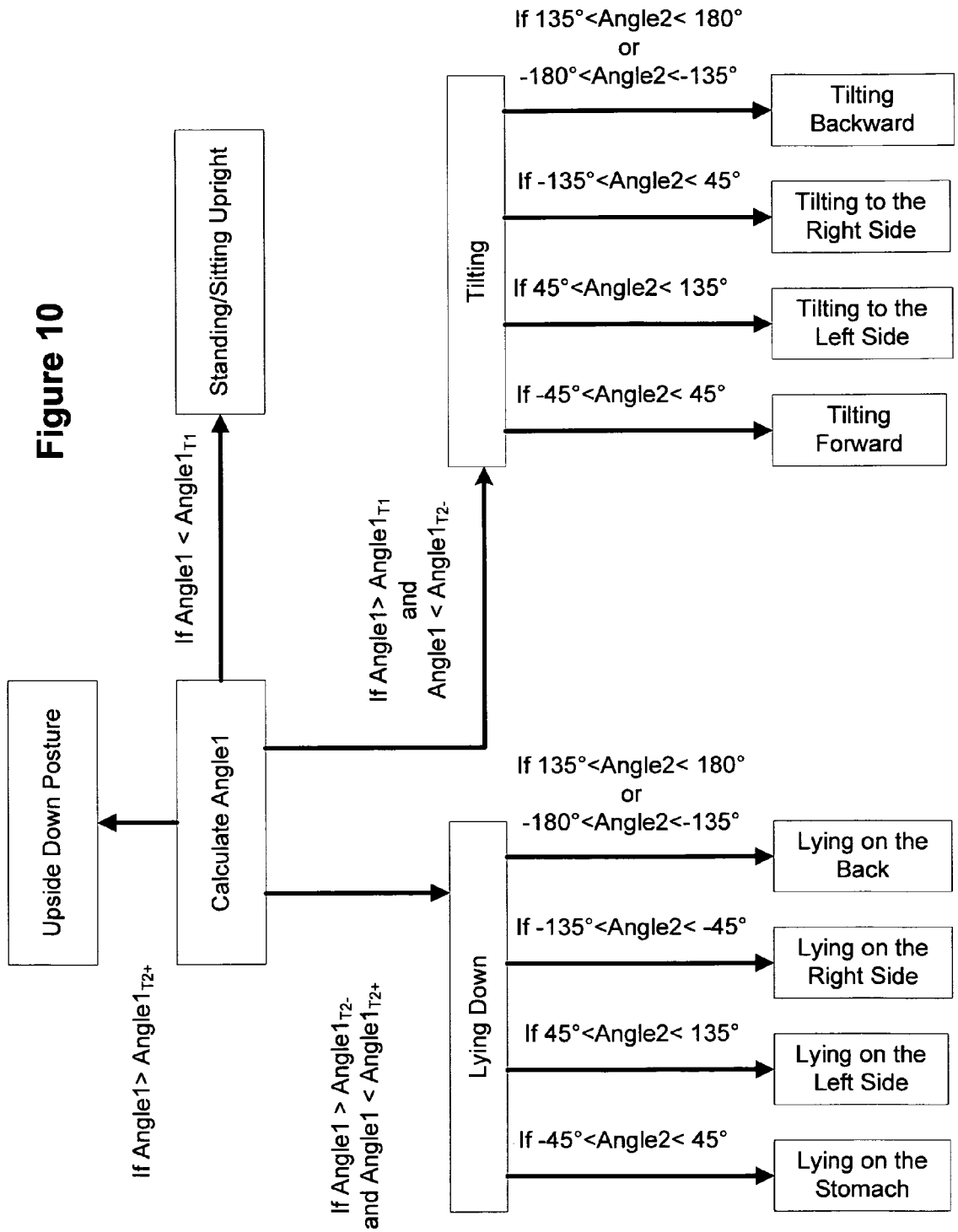
FIG. 10 is a flowchart illustrating a posture detection algorithm in accordance with embodiments of the invention.

FIG. 10 is a flowchart of a posture detection algorithm in accordance with embodiments of the invention. The posture of the patient is determined using threshold angles, Angle1$_{T1}$, Angle1$_{T2-}$ and Angle1$_{T2+}$, and the 45° thresholds on Angle2 as previously described. The angle between the G vector and the Z axis, Angle1, is calculated and is used to initially determine the posture as one of the following postures: upside down, standing/sitting upright, lying down, or tilting. If Angle1 is greater than Angle1$_{T2+}$, then the patient is upside down. If Angle1 is less than Angle1$_{T1}$ then the patient is standing or sitting upright. If Angle1 is greater than Angle1$_{T2-}$ and is less than Angle1$_{T2+}$, then the patient is lying down. If Angle1 is>Angle1$_{T1}$ and Angle1<Angle1$_{T2-}$, then the patient is tilting.

If the patient is lying down, the system uses Angle2 to determine if the patient is lying on the stomach, back, left side or right side. If Angle2 is between −45° and 45° then the patient is lying on the stomach. If Angle2 is between 45° and 135° then the patient is lying on the left side. If Angle2 is between −135° and −45° then the patient is lying on the right side. If Angle2 is between 135° and 180° or between −180° and −135° then the patient is lying on the back.

Similarly, if the patient is tilting down, the system uses Angle2 to determine if the patient is tilting forward, backward, to the left side or to the right side. If Angle2 is between −45° and 45° then the patient is tilting forward. If Angle2 is between 45° and 135° then the patient is tilting to the left side. If Angle2 is between −135° and −45° then the patient is tilting to the right side. If Angle2 is between 135° and 180° or between −180° and −135° then the patient is tilting backward.

Using the calibration process described herein, Angle1 and Angle2 may be calculated with a resolution finer than about 5°. The enhanced resolution of the posture sensing system may be exploited to study the progression or regression of various medical conditions that are associated with certain patient postures. In one implementation, the patient's tilt angle during sleep may be determined and tracked over a period of time. The posture of the patient may be correlated to certain medical conditions, such as disordered breathing, pulmonary disease, and/or congestive heart failure.

In one example, an implantable medical device may determine the patient position and also may detect respiration disturbances such as sleep apnea. A correlation between an increase or decrease in sleep apnea episodes and a particular tilt angle may be determined. The correlation may be made by the implantable device, or information related to tilt angle and respiration disturbance may be telemetered to a remote device, such as an advanced patient management (APM) system for further analysis. Various embodiments described herein may be used in connection with advanced patient management. Methods, structures, and/or techniques described herein relating to advanced patient management, such as those involving remote patient/device monitoring, diagnosis, therapy, or other advanced patient management related methodologies, may incorporate features of one or more of the following references: U.S. Pat. Nos. 6,221,011; 6,277,072; 6,280,380; 6,358,203; 6,368,284; and 6,440,066 each hereby incorporated herein by reference.

In another example, tracking tilt angle over a period of time may be used to track the progression or regression of heart failure. Tracking tilt angle may also be used to assess the effectiveness of heart failure treatments including cardiac resynchronization therapy such as biventricular pacing. Heart failure patients typically have difficulty breathing when they are in a recumbent position. These patients typically sleep using several pillows or other support so that their torso is tilted upward from the prone position.

Tracking the tilt angle during sleep over a period of time provides insight into the severity and progression of heart failure decompensation. For example, if the tilt angle during sleep increases over time, then the patient's heart failure symptoms may be increasing in severity. Conversely, if the tilt angle during sleep decreases over time, heart failure decompensation may be improving. If the patient is receiving treatment for heart failure, such as CRT, then the improvement in heart failure decompensation may be attributed to the therapy. A more detailed description of this process of determining decomposition based on tilt angle detection is described in commonly owned U.S. patent application entitled "Detection of Congestion from Monitoring Patient Response to a Recumbent Position" by Hatlestad, et al., having application Ser. No. 10/267,982, which is hereby incorporated by reference in its entirety.

Embodiments of the posture calibration and posture sensing system illustrated herein are generally described as being implemented in a patient internal device that includes cardiac rhythm management (CRM) circuitry. The CRM circuitry may operate to detect and deliver multi-level therapy for treatment of cardiac arrhythmias. Various types of single and multiple chamber CRM devices may be used to implement a number of electrical stimulation therapies as are known in the art, including pacing therapy, cardioversion and/or defibrillation. The CRM circuitry may operate to provide cardiac resynchronization therapy and may be capable of delivering biventricular pacing therapy for the treatment of congestive heart failure.

It is understood that configurations, features, and combination of features described in the present disclosure can be implemented in a wide range of implantable or external medical devices, and that such embodiments and features are not limited to the particular devices described herein. The systems and methods described herein may be implemented in a wide variety of implantable or external diagnostic and/or therapeutic devices such as defibrillators, cardioverters, pacemakers, cardiac monitors, and resynchronizers, for example.

Figure 11:
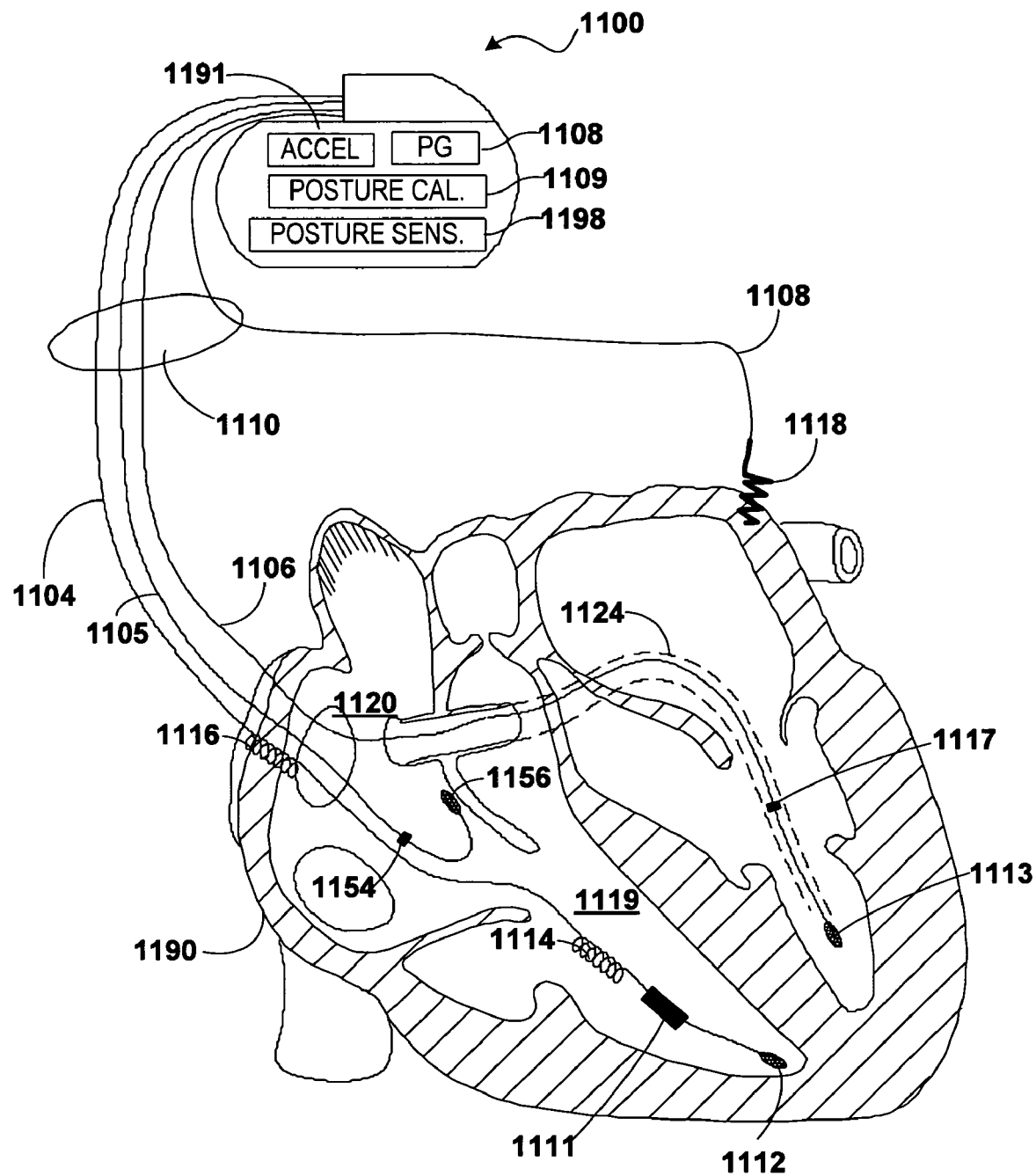
FIG. 11 is a partial view of an implantable device that may include circuitry for implementing portions of a posture detection system in accordance with embodiments of the invention.

Referring now to FIG. 11 of the drawings, there is shown one embodiment of an implantable device that may be used to implement the calibration and posture sensing methods of the present invention. The implantable device 1100 illustrated in FIG. 11 includes a cardiac pulse generator (PG) 1108 electrically and physically coupled to a lead system 1110. The posture calibration 1109 and/or posture sensing 1198 systems of the present invention along with accelerometers 1191 may be disposed within the can of the implantable device 1100.

The housing and/or header of the implantable device 1100 may incorporate one or more electrodes used to provide electrical stimulation energy to the heart and to sense cardiac electrical activity. All or a portion of the implantable device housing may be configured as a can electrode. The implantable device 1100 may include an indifferent electrode positioned, for example, on the header or the housing of the implantable device 1100.

The lead system 1110 is used to detect electrical signals produced by the heart 1190 and to provide electrical energy to the heart 1190 under certain predetermined conditions to treat cardiac arrhythmias. The lead system 1110 may include one or more electrodes used for pacing, sensing, and/or cardioversion/defibrillation. In the embodiment shown in FIG. 7, the lead system 1110 includes an intracardiac right ventricular (RV) lead system 1104, an intracardiac right atrial (RA) lead system 1105, an intracardiac left ventricular (LV) lead system 1106, and an extracardiac left atrial (LA) lead system 1108. The lead system 1110 of FIG. 11 illustrates one embodiment that may be used in connection with the multi level tachyarrhythmia therapy methodologies described herein. Other leads and/or electrodes may additionally or alternatively be used.

The lead system 1110 may include intracardiac leads 1104, 1105, 1106 implanted in a human body with portions of the intracardiac leads 1104, 1105, 1106 inserted into a heart 1190. The intracardiac leads 1104, 1105, 1106 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 11, the lead system 1110 may include one or more extracardiac leads 1108 having electrodes, e.g., epicardial electrodes, positioned at locations outside the heart for sensing and/or pacing one or more heart chambers.

The right ventricular lead system 1104 illustrated in FIG. 11 includes an SVC-coil 1116, an RV-coil 1114, an RV-ring electrode 1111, and an RV-tip electrode 1112. The right ventricular lead system 1104 extends through the right atrium 1120 and into the right ventricle 1119. In particular, the RV-tip electrode 1112, RV-ring electrode 1111, and RV-coil electrode 1114 are positioned at appropriate locations within the right ventricle for sensing and delivering electrical stimulation pulses to the heart. The SVC-coil 1116 is positioned at an appropriate location within the right atrium chamber of the heart 1190 or a major vein leading to the right atrial chamber of the heart 1190.

In one configuration, the RV-tip electrode 1112 referenced to the can electrode may be used to implement unipolar pacing and/or sensing in the right ventricle. Bipolar pacing and/or sensing in the right ventricle may be implemented using the RV-tip 1112 and RV-ring 1111 electrodes. The RV-ring 1111 electrode may optionally be omitted, and bipolar pacing and/or sensing may be accomplished using the RV-tip electrode 1112 and the RV-coil 1114, for example. Sensing in the RV may involve the tip-to-ring vector and the RV-coil to SVC-coil or the RV-coil to SVC coil electrically tied to the can vector. The right ventricular lead system 1104 may be configured as an integrated bipolar pace/shock lead. The RV-coil 1114 and the SVC-coil 1116 are defibrillation electrodes.

The left ventricular lead 1106 includes an LV distal electrode 1113 and an LV proximal electrode 1117 located at appropriate locations in or about the left ventricle for pacing and/or sensing the left ventricle. The left ventricular lead 1106 may be guided into the right atrium of the heart via the superior vena cava. From the right atrium, the left ventricular lead 1106 may be deployed into the coronary sinus ostium, the opening of the coronary sinus. The lead 1106 may be guided through the coronary sinus to a coronary vein 1124 of the left ventricle. This vein is used as an access pathway for leads to reach the surfaces of the left ventricle that are not directly accessible from the right side of the heart. Lead placement for the left ventricular lead 1106 may be achieved via subclavian vein access and a preformed guiding catheter for insertion of the LV electrodes 1113, 1117 adjacent to the left ventricle.

Unipolar pacing and/or sensing in the left ventricle may be implemented, for example, using the LV distal electrode 1113 referenced to the can electrode. The LV distal electrode 1113 and the LV proximal electrode 1117 may be used together as bipolar sense and/or pace electrodes for the left ventricle. The left ventricular lead 1106 and the right ventricular lead 1104, in conjunction with the PG 1108, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 1105 includes a RA-tip electrode 1156 and an RA-ring electrode 1154 positioned at appropriate locations in the right atrium for sensing and pacing the right atrium. In one configuration, the RA-tip 1156 referenced to the can electrode, for example, may be used to provide unipolar pacing and/or sensing in the right atrium 1120. In another configuration, the RA-tip electrode 1156 and the RA-ring electrode 1154 may be used to effect bipolar pacing and/or sensing.

FIG. 11 illustrates one embodiment of a left atrial lead system 1108. In this example, the left atrial lead 1108 is implemented as an extracardiac lead with an LA distal electrode 1118 positioned at an appropriate location outside the heart 1190 for sensing and pacing the left atrium. Unipolar pacing and/or sensing of the left atrium may be accomplished, for example, using the LA distal electrode 1118 to the can pacing vector. The left atrial lead 1108 may be provided with additional electrodes used to implement bipolar pacing and/or sensing of the left atrium.

Figure 12:
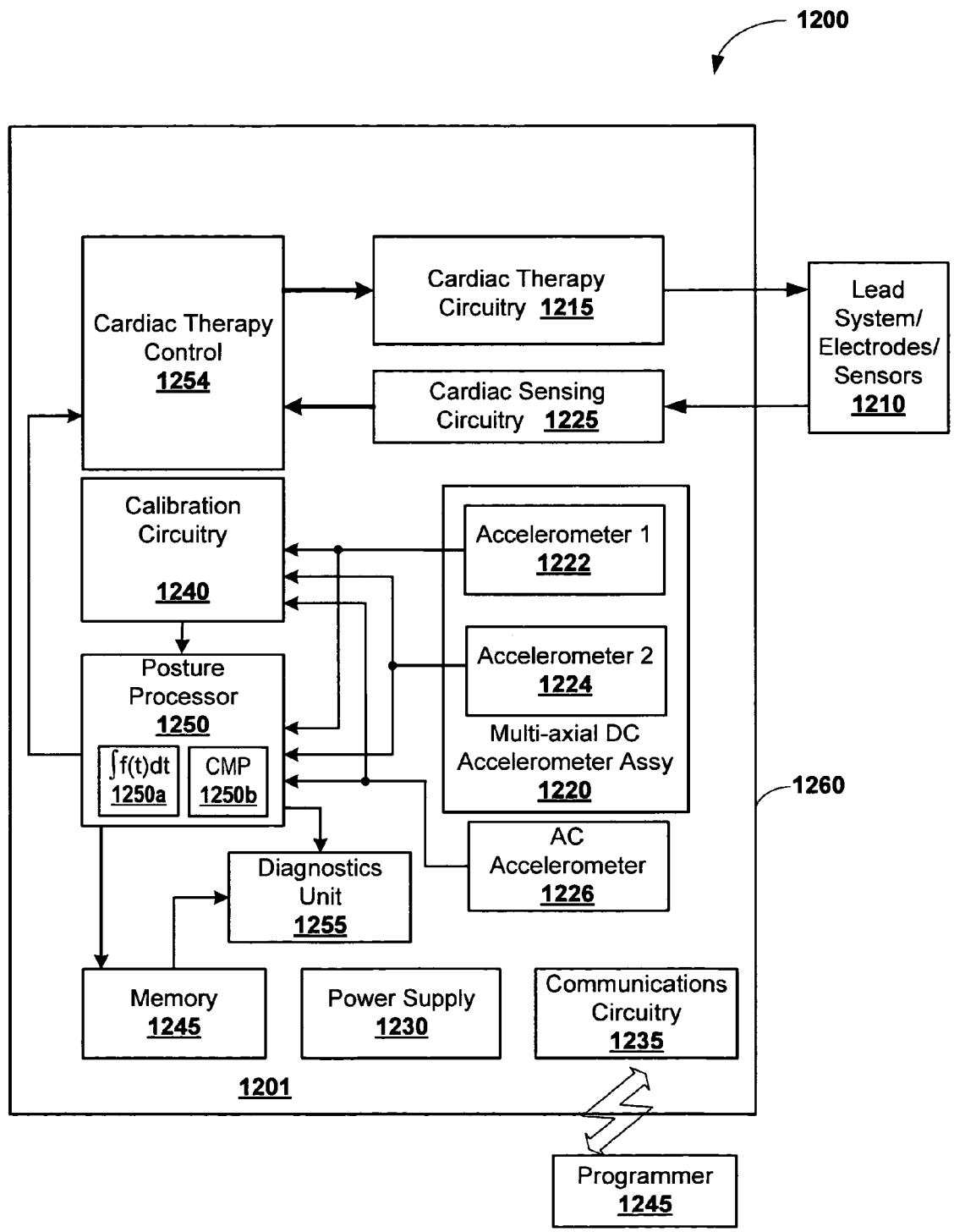
FIG. 12 is a block diagram of an implantable device illustrating possible components of a posture detection system in accordance with embodiments of the invention.

Referring now to FIG. 12, there is shown a block diagram of an embodiment of an implantable device 1200 suitable for implementing posture calibration and/or posture sensing methodologies of the present invention. FIG. 12 shows the implantable device 1200 divided into functional blocks. There exist many possible configurations in which these functional blocks can be arranged. The example depicted in FIG. 12 is one possible functional arrangement. The implantable device 1200 depicted in FIG. 12 includes CRM circuitry including cardiac sensing circuitry for receiving cardiac signals from a heart and delivering electrical energy in the form of pace pulses or cardioversion/defibrillation pulses to the heart.

The housing of the implantable device encloses a multi-axis orientation sensor assembly 1220, comprising, for example, two DC uniaxial accelerometers 1222, 1224. The sensor assembly 1220 may also have other internal or external signal conditioning circuitry (not shown) coupled to the accelerometers 1222, 1224, such as high pass and low pass filters. The sensitive axes of the uniaxial accelerometers 1222, 1224 are typically positioned to be mutually orthogonal along the W and V axes as described above. When the device 1200 is implanted within the patient's body, the accelerometers 1222, 1224 produce signals corresponding to the orientation of the device with respect to the earth's gravitational force. In addition, an AC accelerometer 1226 is aligned along the third axis (e.g., the U axis) and measures dynamic acceleration in this direction.

The outputs of the accelerometers 1222, 1224, 1226 may be coupled to calibration circuitry 1240 used to perform posture calibration according to the methods of the present invention. The outputs of the accelerometers 1222, 1224, 1226 and the calibration circuitry 1240 may also be coupled to a posture processor 1250. The posture processor 1250 may be used to determine patient position including tilt angle in accordance with the posture determination methodologies of the present invention described herein.

The posture processor 1250 may be implemented using general-purpose, programmable microprocessors or custom digital and/or analog circuitry. The posture processor 1250 may be able to access registers of a memory 1245 for storing and retrieving acceleration values and other data of interest. The posture processor 1250 may include circuitry and/or instructions for performing various functions known in the art that are applicable to the present invention. For example, the posture processor 1250 may include an integrator 1250*a* for integrating outputs of the AC accelerometer 1226 during periods of unsteady-state acceleration. The posture processor 1250 may also include a comparator 1250*b* for determining steady-state conditions by comparing signals sensed via the DC accelerometer assembly against an AC threshold. Similarly, the comparator 1250*b* may be used for determining acceleration vector directions in the axis of the AC accelerometer based on comparing integrated AC values with thresholds as discussed in relation to FIG. 6.

In the embodiment illustrated in FIG. 12, the posture detector, including the accelerometers 1222, 1224, 1226, calibration circuitry 1240 and posture processor 1250 are disposed within the housing of the implantable device 1260 along with CRM circuitry. A cardiac lead system 1210 may be implanted so that cardiac electrodes are electrically coupled to the heart tissue as described above in connection with FIG. 11. The cardiac electrodes of the lead system 1210 along with sensing circuitry 1225 disposed within the implantable device housing are used to sense cardiac signals associated with electrical activity of the heart.

The cardiac electrodes and lead system 1210 may also be used to deliver electrical stimulation pulses or shocks generated by the cardiac therapy circuitry 1215 to the heart for treating various cardiac arrhythmias. The CRM circuitry, including the therapy control circuitry 1254, cardiac sensing circuitry 1225, cardiac therapy circuitry 1215, and cardiac electrodes/lead system 1210, may detect cardiac signals and deliver therapeutic electrical stimulation to any of the left and right ventricles and left and right atria, for example. In some implementations, the therapy control circuitry may use posture information to modify therapy delivered to the patient. For example, if the posture information indicates the patient is lying down and sleeping, the rate of pacing pulses may be delivered as a sleep pacing rate that is different from the pacing rate delivered while the patient is upright and awake.

Power to the implantable device 1260 is supplied by an electrochemical battery 1230 that is housed within the implantable device 1260. The implantable device 1260 may also include various forms of memory 1245. The memory 1245 may be used to store posture information for tracking changes in patient posture over time. In some implementations, the implantable device 1260 may incorporate a diagnostics processor 1255 that utilizes posture information stored in memory 1240, possibly along with other information, to detect the presence or track the progression of various medical disorders. In another implementation, the diagnostics processor is incorporated in a remote patient external device. The posture information, along with other parameters and data stored in the memory 1240, may be transmitted via telemetry to an external programmer unit 1245 or other patient-external device, as desired.

Communications circuitry 1235 allows the implantable device 1260 to communicate with an external programmer unit 1245 and/or other patient-external system(s). In one embodiment, the communications circuitry 1235 and the programmer unit 1245 use a wire loop antenna and a radio frequency telemetric link to receive and transmit signals and data between the programmer 1245 and communications circuitry 1235. In this manner, programming commands and/or other information may be transferred to the implantable device 1260 from the programmer 1245 during and after implant.

A number of the examples presented herein involve block diagrams illustrating functional blocks used for in accordance with embodiments of the present invention. It will be understood by those skilled in the art that there exist many possible configurations in which these functional blocks can be arranged and implemented.

The examples depicted herein provide examples of possible functional arrangements used to implement the approaches of the invention. The components and functionality depicted as separate or discrete blocks/elements in the figures in general can be implemented in combination with other components and functionality. The depiction of such components and functionality in individual or integral form is for purposes of clarity of explanation, and not of limitation. It is also understood that the components and functionality depicted in the Figures and described herein can be implemented in hardware, software, or a combination of hardware and software.

Methods, devices, and systems in accordance with the present invention may incorporate one or more of the features, structures, methods, or combinations thereof described herein. For example, a medical system may be implemented to include one or more of the features and/or processes described herein. It is intended that such a method, device, or system need not include all of the features and functions described herein, but may be implemented to include one or more selected features and functions that provide unique structures and/or functionality.

Various modifications and additions can be made to the preferred embodiments discussed hereinabove without departing from the scope of the present invention. Further, although the present description is related to medical device uses, it will be appreciated that similar sensing circuitry may be used in other medical, industrial, or military applications that may require the measurement of device or body orientation. Accordingly, the scope of the present invention should not be limited by the particular embodiments described above, but should be defined only by the claims set forth below and equivalents thereof.

What is claimed is:

1. A method, comprising:
    detecting orientations of a body with respect to first and second axes;
    detecting movement of the body with respect to a third axis; and
    determining a three-dimensional orientations of the body based on the orientations and the movement.

2. The method of claim 1, further comprising detecting steady-state acceleration conditions of the body with respect to the first and second axes.

3. The method of claim 2 wherein the determining the three-dimensional orientations of the body comprises determining the three-dimensional orientations of the body for the steady-state acceleration conditions.

4. The method of claim 3, wherein determining the three-dimensional orientations of the body comprises determining a sign of the three-dimensional orientations with respect to the third axis based on transitions between the steady-state acceleration conditions.

5. The method of claim 1, wherein determining the three-dimensional orientations of the body comprises calculating a magnitude component of the three-dimensional orientations with respect to the third axis using magnitude components of the three-dimensional orientations with respect to the first and second axes.

6. The method of claim 1, wherein detecting the orientation of the body with respect to the first and second axes comprises detecting the orientation using one or more sensors responsive to the earth's gravitational field.

7. The method of claim 1, wherein detecting orientations of a body with respect to first and second axes comprises detecting the orientation using one or more DC accelerometers.

8. The method of claim 7, further comprising determining steady-state acceleration conditions of the body with respect to the first and second axes using AC components extracted from signals of the DC accelerometers.

9. The method of claim 1, wherein detecting the movement of the body comprises detecting the movement using one or more AC accelerometers.

10. The method of claim 1, wherein at least two of the first, second, and third axes are substantially orthogonal.

11. The method of claim 1, wherein at least two of the first, second, and third axes are non-orthogonal.

12. The method of claim 1, wherein the body is a patient's body, and at least one of detecting the orientations, detecting the movement, and determining the three-dimensional orientations are performed at least in part implantably.

13. The method of claim 1, further comprising controlling a medical device based on the three-dimensional orientations of the body.

14. The method of claim 13, wherein the controlling a medical device comprises controlling a cardiac rhythm management device.

15. The method of claim 1, wherein the body is a patient's body, and further comprising tracking patient well-being at least in part using the three-dimensional orientations of the patient's body.

16. The method of claim 1, wherein the body is a patient's body, and further comprising detecting a patient disorder based at least in part on the three-dimensional orientations of the patient's body.

17. An apparatus, comprising:
    first and second sensors responsive to a gravitational field, the first and second sensors disposed along respective first and second axes of the apparatus;
    a movement sensor disposed along a third axis of the apparatus;
    sensing circuitry coupled to the first and second sensors and the movement sensor, the sensing circuitry configured to,
        determine orientations of the apparatus with respect to the first and second axes of the apparatus based on outputs of the first and second sensors;
        determine movements of the apparatus based on outputs of the movement sensor; and
        determine three-dimensional orientations of the apparatus based on the orientation and the movements.

18. The apparatus of claim 17, wherein the sensing circuitry is further configured to detect steady-state acceleration conditions of the apparatus and determining the three-dimensional orientations of the apparatus for the steady-state acceleration conditions.

19. The apparatus of claim 17, further comprising control circuitry coupled to the sensing circuitry and configured to receive the three-dimensional orientations of the apparatus and control the apparatus based on the three-dimensional orientations.

20. The apparatus of claim 19, further comprising implantable cardiac rhythm management circuitry coupled to the control circuitry and configured to adjust a pacing provided by the implantable cardiac rhythm management circuitry based on the three-dimensional orientations of the apparatus received via the control circuitry.

21. The apparatus of claim 17, wherein at least two of the first, second, and third axes of the apparatus are substantially orthogonal.

22. The apparatus of claim 17, wherein the apparatus comprises an implantable medical device.

23. The apparatus of claim 17, wherein the sensing circuitry is configured to determine acceleration magnitudes along the third axis based on acceleration magnitudes detected via the first and second sensors.

24. The apparatus of claim 23, wherein the sensing circuitry is configured to determine acceleration directions along the third axis based on successive determinations of the acceleration magnitudes along the third axis measured during subsequent steady-state acceleration periods.

25. The apparatus of claim 17, wherein one or more of the first and second sensors comprise DC accelerometers.

26. The apparatus of claim 17, wherein the movement sensor comprises one or more AC accelerometers.

27. The apparatus of claim 17, wherein the apparatus is implanted in a patient's body, and wherein the sensing circuitry is configured to determine an orientation of the patient's body based on the three-dimensional orientations of the apparatus.

28. A posture sensing system comprising:
    means for detecting orientations of a body with respect to first and second axes;
    means for detecting movement of the body with respect to a third axis; and
    means for determining a three-dimensional orientation of the body based on the orientation and the movement.

29. The posture sensing system of claim 28, further comprising means for detecting steady-state acceleration conditions of the body for purposes of determining the three-dimensional orientation of the body during the steady-state acceleration conditions.

* * * * *

UNITED STATES PATENT AND TRADEMARK OFFICE
CERTIFICATE OF CORRECTION

PATENT NO. : 7,471,290 B2
APPLICATION NO. : 11/283489
DATED : December 30, 2008
INVENTOR(S) : Hua Wang et al.

It is certified that error appears in the above-identified patent and that said Letters Patent is hereby corrected as shown below:

In the Claims

Column 17, Claim 1, line 41: "determining a three-dimensional" should be --determining three-dimensional--.

Column 17, Claim 6, line 61: "orientation" should be --orientations--; and line 63: "orientation" should be --orientations--.

Column 17, Claim 7, line 67: "orientation" should be --orientations--.

Column 18, Claim 17, line 46: "orientation" should be --orientations--.

Column 18, Claim 18, line 49: "determining" should be --determine--.

Column 20, Claim 28, line 10: "orientation" should be --orientations--.

Signed and Sealed this

Thirty-first Day of March, 2009

JOHN DOLL
*Acting Director of the United States Patent and Trademark Office*